United States Patent [19]

van den Engh et al.

[11] Patent Number: 5,747,349
[45] Date of Patent: May 5, 1998

[54] FLUORESCENT REPORTER BEADS FOR FLUID ANALYSIS

[75] Inventors: Ger van den Engh; Bernhard H. Weigl, both of Seattle, Wash.

[73] Assignee: University of Washington, Seattle, Wash.

[21] Appl. No.: 621,170

[22] Filed: Mar. 20, 1996

[51] Int. Cl.$^6$ .................. G01N 33/00; G01N 21/01; G01N 21/64

[52] U.S. Cl. .................. 436/172; 356/246; 422/81; 422/82.05; 422/82.08; 422/82.09; 436/8; 436/10; 436/43; 436/52; 436/63; 436/68; 436/73; 436/79; 436/80; 436/81; 436/82; 436/83; 436/84; 436/86; 436/87; 436/91; 436/100; 436/103; 436/127; 436/136

[58] Field of Search .................. 436/8, 10, 43, 436/52, 63, 68, 73, 79–84, 86–88, 91–101, 103, 104, 124, 127, 128–132, 136, 164, 172, 183; 356/246; 422/81, 82.05, 82.08, 82.09

[56] References Cited

U.S. PATENT DOCUMENTS

| | | | |
|---|---|---|---|
| 4,125,376 | 11/1978 | Razulis | 436/79 |
| 4,245,907 | 1/1981 | Rosen | 356/244 |
| 4,269,516 | 5/1981 | Lubbers et al. | 356/427 |
| 4,577,109 | 3/1986 | Hirschfeld | 250/461.1 |
| 4,609,689 | 9/1986 | Schwartz et al. | 523/202 |
| 4,762,799 | 8/1988 | Seitz et al. | 436/79 |
| 4,823,168 | 4/1989 | Kamahori et al. | 356/246 |
| 4,907,037 | 3/1990 | Boisde et al. | 356/412 |

(List continued on next page.)

FOREIGN PATENT DOCUMENTS

| | | |
|---|---|---|
| 0 345 782 | 12/1989 | European Pat. Off. . |
| 0 475 045 A1 | 3/1992 | European Pat. Off. . |
| 0 519 198 A2 | 12/1992 | European Pat. Off. . |
| 4140411 | 6/1993 | Germany . |
| 91/13338 | 9/1991 | WIPO . |
| 91/15750 | 10/1991 | WIPO . |
| 92/07245 | 4/1992 | WIPO . |

OTHER PUBLICATIONS

L.A. Saari et al. *Anal. Chem.* 1982, 54, 821–823.
R. Migliering *Biol. Cell* 1986, 58, 127–130.
M. Fechheimer et al. *Eur. J. Cell Biol.* 1986, 40, 242–247.
Z. Zhujun et al. *Anal. Chim. Acta* 1986, 184, 251–258.
M.-R.S. Fuh et al. *Analyst* 1987, 112, 1159–1163.
T.C. Werner et al. *Anal. Chem.* 1989, 61, 211–215.
P. Judex *Kernforschungszent Karlsruhe KFK* 1991, KFK 4863.
E. Verpoorte et al. *Sens. Actuators B* 1992, Bb, 66–70.
P. Heilmann et al. *Environ. Health Perspect.* 1992, 97, 115–120.
Y. Kikuchi et al. *Microvasc. Res.* 1992, 44, 226–240.
D.J. Harrison et al. *Sens. Actuators B* 1993, B10, 107–116.
R.B. Thompson et al. *Anal. Chem.* 1993, 65, 853–856.
A. Rumphorst et al. *J. Fluoresc.* 1994, 4, 45–48.

(List continued on next page.)

*Primary Examiner*—Arlen Soderquist
*Attorney, Agent, or Firm*—Greenlee, Winner & Sullivan, P.C.

[57] ABSTRACT

The present invention provides a method and apparatus for rapid measurement of a fluid bulk analyte, requiring only microscale volumes. Several fluid bulk analytes can be measured simultaneously and, for biological samples, the cell content can also be measured simultaneously. The invention comprises reporter beads for chemical analysis of fluid bulk properties such as pH, oxygen saturation and ion content. Each reporter bead comprises a substrate bead having a plurality of at least one type of fluorescent reporter molecules immobilized thereon. The fluorescent properties of the reporter bead are sensitive to a corresponding analyte. Reporter beads are added to a fluid sample and the analyte concentration is determined by measuring fluorescence of individual beads, for example in a flow cytometer. Alternatively, reporter molecules which change absorbance as a function of analyte concentration can be employed.

47 Claims, 5 Drawing Sheets

U.S. PATENT DOCUMENTS

| | | | |
|---|---|---|---|
| 4,908,112 | 3/1990 | Pace | 204/299 R |
| 4,983,038 | 1/1991 | Ohki et al. | 356/246 |
| 5,055,694 | 10/1991 | Jeffers et al. | 250/458.1 |
| 5,073,497 | 12/1991 | Schwartz | 436/8 |
| 5,219,763 | 6/1993 | Van Hoegaerden | 436/523 |
| 5,288,642 | 2/1994 | Turner | 436/8 |
| 5,498,392 | 3/1996 | Wilding et al. | 422/68.1 |
| 5,587,128 | 12/1996 | Wilding et al. | 422/50 |
| 5,593,838 | 1/1997 | Zanzucchi et al. | 435/6 |
| 5,599,503 | 2/1997 | Manz et al. | 422/82.05 |

OTHER PUBLICATIONS

N.F. Johnson *Environ. Health Perspect*, 1994, 102 Suppl 5, 97–102.

A.T. Woolley et al. *Proc. Natl. Acad. Sci. USA* 1994, 19, 11348–11352.

Miyake R. et al. (1991), "A Development of Micro Sheath Flow Chamber," Proc. IEEE Micro Electro Mechanical Systems, Nara, Japan, 30 Jan.–Feb. 1991, 6 pp.

Shapiro, H.M. and Hercher, M. (1986), "Flow Cytometers Using Optical Waveguides in Place of Lenses for Specimen Illumination and Light Collection," *Cytometry* 7:221–223.

Sobek, D. et al. (1993), "A Microfabricated Flow Chamber for Optical Measurements in Fluids," Proc. IEEE, Micro Electro Mechanical Systems, Fort Lauderdale, FL, Feb. 7–10, 1993, pp. 219–224.

Sobek, D. et al. (1994), "Microfabricated Fused Silica Flow Chambers for Flow Cytometry," Solid–State Sensor and Actuators Workshop, Hilton Head, SC, Jun. 13–16, 1994, 4 pp.

Wilding, P. et al. (1994), "Manipulation and Flow of Biological Fluids in Straight Channels Micromachined in Silicon," *Clin. Chem.* 40(1):43–47.

Wilson, M.R. et al., "Immunofluorescent Labeling Using Covalently Linked Anti–Phycoerythrin Antibodies and Phycoerthrin Polymers," *Cytometry* (1991) 12:373–377.

Kim, K. et al., "Solid–phase immunoassay using a flow cytometer: quantitative and qualitative determination of protein antigens and a hapten," *Immunology Letters* (1992) 31:267–272.

Haughland, Richard P., "Physiological Indicators and Tracers," *Molecular Probes, Handbook of Fluorescent Probes and Research Chemicals*, 5th Ed., 1992–1994, K.D. Larison, Ed., Eugene, OR, pp. 111–152.

Haugland, Richard P., "Fluorescent Latex Microspheres," *Molecular Probes, Handbook of Fluorescent Probes and Research Chemicals*, 5th Ed., 1992–1994, K.D. Larison, Ed., Eugene, OR, pp. 193–200.

Rohr, E.L. and Kaffenberger, W., "Fluorescence Instability of Propidium Iodide–Labelled Microspheres in (Para)Formaldehyde," *Cytometry* (1993) 14:584–586.

Weigl, B.H. and Wolfbeis, O.S., "Capillary Optical Sensors," *Analytical Chemistry* (1994) 66(20):3323–3327.

Renner, E.D., "Development and Clinical Evaluation of an Amplified Flow Cytometric Fluoroimmunoassay for *Clostridium difficile* Toxin A," *Cytometry* (1994) 18:103–108.

FLUORESCENT REPORTER BEADS FOR FLUID ANALYSIS

This invention was made with support under Army research contract DAMD17-94-J-4460 awarded by the U.S. Army. The government has certain rights in the invention.

FIELD OF THE INVENTION

This invention relates to fluorescent reporter beads for flow-cytometric measurement of analytes in a fluid bulk.

BACKGROUND OF THE INVENTION

In clinical analysis of blood, medical practitioners typically request the red blood cell volume and blood count, the pH, and the concentrations of albumin, bilirubin, salt ions, and dissolved $CO_2$ and $O_2$. The analysis is typically carried out on a macroscale (ml volume range) using several separate tests, each requiring different reagents and apparatus. Red blood cell volume is determined by spinning the sample to separate the serum. The pH, albumin, and ions such as $Ca^{+2}$ and $Cl^-$ are analyzed by adding appropriate indicator dyes and measuring the absorption. Alternatively, ion sensitive electrodes can be employed.

Properties of the fluid bulk, such as pH and salt content, can also be measured by adding to the fluid a fluorescent dye which is sensitive to the specific analyte. This is generally practiced in research laboratories as opposed to clinical laboratories. Quantitative analysis requires accurate measurement of the volume of the sample fluid and of the dye in order to know (1) the number of dye molecules added and (2) the amount of dilution of the sample fluid. Therefore blood analysis by this technique requires macroscale volumes; on a microscale ($\leq \mu l$ range) the error in volume measurements is too large.

Optical flow cytometry allows microscale measurement of individual cells or other particles in a fluid stream as they pass single file through a measurement zone. Using laser illumination, the small angle scattering, large angle scattering and fluorescence can be measured. From the scattering, the size and shape of the cells can be obtained, thus distinguishing between red and white blood cells. By the use of specific fluorochromes, a wide range of cellular properties can be measured, including DNA content, protein content, antigens, surface sugars, membrane structure, intracellular $Ca^{+2}$, and intracellular pH (see, for example, H. M. Shapiro, *Practical Flow Cytometry*, 3rd edition, Wiley-Liss, New York, 1995). However flow cytometry measures properties of cells in a fluid stream; it does not measure properties, such as pH and salt content, of the fluid bulk which forms the stream.

Fluorescent beads (microspheres), comprising beads impregnated with fluorescent dye, are commonly used in flow cytometry as fluorescence calibration standards. Fluorescent beads can also be used to trace phagocytosis. In immuno-assays, antibody (antigen) coated fluorescent beads can be used to detect the corresponding antigen (antibody) in a cell or on a cell surface. In this case the bead contains a fluorescent dye and additionally contains an immunoreactive group which functions to attach the bead to a cell. The fluorescence intensity of the cell is a function of the number of beads attached to the cell and therefore of the number of reactive sites on the cell. Similarly antigens in the fluid can be detected by the aggregation of antibody coated fluorescent beads. In immuno-assays in flow cytometers it is the number of beads on the cell or in the aggregate which determines the measured fluorescence intensity; the fluorescence intensity of each individual bead is unchanged.

Both the macroscale and microscale techniques described above suffer disadvantages for use in blood analysis. The macroscale analysis requires ml range volumes of blood and separate tests for each analyte. The flow cytometer can use $\mu l$ volumes and can simultaneously measure more than one property, but it measures the cell properties, not the composition of the fluid bulk.

SUMMARY OF THE INVENTION

The present invention provides a method and apparatus for rapid measurement of a fluid bulk analyte, requiring only microscale volumes. Several fluid bulk analytes can be measured simultaneously and, for biological samples, the cell content can also be measured simultaneously.

The invention comprises reporter beads for chemical analysis of fluid bulk properties such as pH, oxygen saturation and ion content. Each reporter bead comprises a substrate bead having a plurality of at least one type of fluorescent reporter molecules immobilized thereon. A fluorescent property of the reporter bead, such as intensity, lifetime or wavelength, is sensitive to a corresponding analyte. Reporter beads are added to a fluid sample and the analyte concentration is determined by measuring fluorescence of individual beads, for example in a flow cytometer. Alternatively, reporter molecules which change absorbance as a function of analyte concentration can be employed.

Several advantages are provided by the reporter beads of this invention. Because the reporter molecules are concentrated on particles rather than in a fluid, dilution of the sample fluid is minimal and accurate measurement of the sample volume is not required. Because the fluorescence of individual beads is measured rather than the fluorescence of the whole sample, the number of beads added need not be precisely determined. The measurement does not require incubation, washing, or filtering steps; reporter beads can be mixed with a fluid sample and the fluorescence measured without further processing. Because the reporter molecules are immobilized on substrate beads, incompatibilities between different types of reporter molecules are removed. Beads tagged with different reporter molecules can be mixed within one sample and a plurality of analytes can be measured simultaneously. The present invention can be utilized in combination with other flow cytometric measurements known in the art. For example, light scattering can be measured simultaneously to determine cell size and shape. Light scattering can also be used to distinguish between different sizes of reporter beads.

For convenient, error-free use, the reporter beads of this invention can be packaged in a bead cartridge. The cartridge is inserted in the fluid inlet of the flow cytometer and the beads are mixed with the fluid before fluorescence measurement. This technique can be utilized because, with the reporter beads of this invention, pre-analysis processing steps are not required and because neither the sample volume nor the bead concentration need be determined precisely.

A disposable flow cytometer flow module having an integral bead cartridge is a further aspect of this invention. The flow module has a micromachined flow channel with fluid inlet and outlet ports. The preferred flow module contains a V-groove flow channel etched into a silicon wafer. For measurement, the flow module is attached to a flow cytometer optical head having an excitation laser and a fluorescence detector.

In addition to blood analysis, the reporter beads of this invention can be used to analyze a wide range of other fluids.

For example, they can be used to determine water purity downstream of a manufacturing facility or waste treatment plant. They can be used in food or beverage processing, for example beer brewing, to monitor fluid constituents and to check for contamination. Analytes which can be measured using reporter beads of this invention include pH, $O_2$, $CO_2$, $Ca^{+2}$, $Na^+$, $K^+$, $Cl^-$, other halides, $Mg^{+2}$, $Zn^{+2}$, $Tb^{+3}$, and other metal ions including alkali and alkaline-earth ions, ionic strength, solvent polarity, albumin, alcohols, pesticides, organic salts such as lactate, sugars such as glucose, heavy metals, and drugs such as salicylic acid, halothane and narcotics.

DETAILED DESCRIPTION OF THE INVENTION

Figure 1:
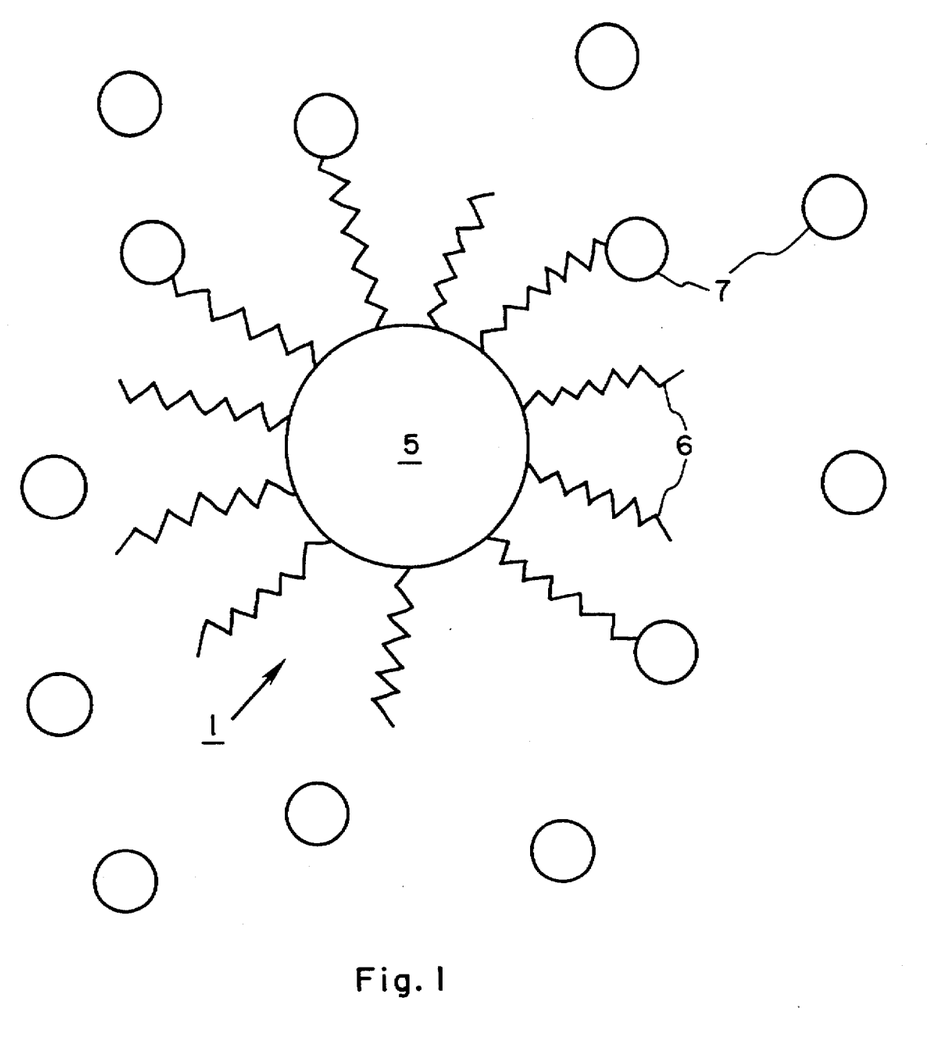
FIG. 1 shows a reporter bead.

The invention provides reporter beads for chemical analysis of fluid bulk properties as shown in FIG. 1. Each reporter bead 1 comprises a substrate bead 5 having a plurality of fluorescent reporter molecules of a first type 6 immobilized thereon. The fluorescence of the reporter molecules is sensitive to the concentration of analyte 7. The term substrate bead is used herein for a particle which can be dispersed in a sample fluid and which can immobilize reagents, separate from the sample fluid. The term reporter molecule is used herein for a fluorescent molecule having fluorescence properties which are a function of the concentration of a particular analyte or class of analytes. The term type of reporter molecule refers to a specific chemical composition (as opposed to a class of molecules) and is used to distinguish between a plurality of molecules of a given type and a plurality of types of molecules. The term fluid bulk is used herein for that part of a fluid which is outside of cells or particles dispersed therein.

The reporter molecules of this invention can be any fluorescent molecules having fluorescence properties which are a function of the concentration of a particular analyte or class of analytes. Many dyes and fluorochromes known in the art can be used as reporter molecules in this invention (see, for example, R. P. Haugland, *Handbook of Fluorescent Probes and Research Chemicals*, 5th Edition, Molecular Probes Inc., Eugene, 1992). The criteria for reporter molecule selection are that the molecules can be immobilized on a substrate bead and that their fluorescence is a function of the concentration of an analyte. In contrast with previously used fluorescent beads, wherein the number of beads in an aggregate changes, in the present invention the fluorescence of each individual bead changes. In further contrast, the reporter beads of this invention are not required to have an immunoreagent, such as a ligand, antiligand, antigen or antibody, on the surface in combination with the reporter molecules. Examples of preferred reporter beads are listed in Table I.

The reporter molecules interact with the analyte in a way that changes the fluorescent properties of the reporter molecule. In some instances the reporter molecule reacts with the analyte, as in the case of albumin detection by AB 580 (Molecular probes). In some cases the interaction is not a chemical reaction. For example the reporter molecule fluorescence can be quenched by nonradiative energy transfer to the analyte, as in the case of $O_2$ detection by ruthenium diphenyl phenanthroline. For some reporter molecules the fluorescence is sensitive to polarity changes in the fluid, which can be used to detect organic solvents and hydrocarbons within an aqueous fluid. The interaction can also be through other solvent effects, wherein the ionic strength of the solvent affects the fluorescence. Solvent effects can be used to determine the total concentration of all dissolved ions. The interaction need not be a ligand/antiligand or antigen/antibody reaction. The interaction preferably does not lead to an aggregate with other particles and, in particular, does not create an aggregate containing a plurality of reporter beads. It is preferred that the interaction of the analyte with the reporter molecules does not significantly perturb the analyte concentration in the fluid.

The response time of the reporter molecule/analyte interaction is preferably on the scale of seconds or less so that the reporter beads can be mixed with the sample fluid and the fluorescence measured without delay. In the examples of Table I the response times are on the msec scale. Useful reporter molecules can also have response times on the scale of minutes or longer, but rapid response is preferred.

At least one fluorescence property of the reporter molecules is a function of analyte concentration. The property measured for the reporter beads of this invention can be any property which is affected by the analyte interaction, such as the fluorescence intensity, decay time or spectrum. Some reporter molecules have two fluorescence bands and the ratio of the emissions at the two bands depends on the analyte concentration. Some calibration beads known in the art are incidentally sensitive to fluid properties such as pH, dissolved oxygen and solvent polarity. In the art, this has been treated as an undesirable side effect and efforts have been made to minimize this source of error. In contrast, the sensitivity of the reporter molecule to the analyte preferably gives greater than a 10% change, and more preferably greater than a 50% change, in at least one fluorescence property over the analytic range of analyte concentration. For example, in measuring the pH of blood, the fluorescence preferably changes by at least 10% over the pH range of 6.8–7.8. The optimum sensitivity provides about a 90% change over the analytical range. Preferably the fluorescence of the reporter molecules is sensitive only to a specific analyte or class of analytes. The measured fluorescence is a function of the concentration of the analyte. To get the absolute concentration, calibration using a fluid with known concentration can be employed. Without calibration, the relative concentration is obtained.

Alternatively, the reporter molecules can be absorption indicators, for example the physiological pH indicator N9 (Merck, Germany), immobilized on a substrate bead. Such indicators change their absorption as a function of analyte concentration. Typically the color of the molecules changes (i.e., the wavelength of their absorption maximum). Reporter beads with immobilized absorption indicators can be measured in two ways: if the substrate beads are clear, then the absorption of the reporter beads can be measured in transmission; if the substrate beads are opaque, then the diffuse reflectance from the reporter bead is measured at a relatively small angle to the incident light beam (0°–90°). In order to compensate for the effect of bead size variations on scattering, the diffuse reflectance or transmission can additionally be measured using a light beam of a reference wavelength which is not affected by the interaction of the indicator dye with the analyte. This invention is described below with respect to fluorescent reporter beads. Modifications for absorptive reporter beads will be apparent to those skilled in the art. Absorptive reporter molecules can be used in combination with fluorescent reporter molecules on a substrate bead, and absorptive beads can be used in combination with fluorescent beads.

The substrate bead function is to immobilize the reporter molecules. The reporter molecules can be on the surface of or within the substrate bead. The beads can be fabricated from a variety of materials and can have any shape, not limited to spherical. Suitable materials include glass, latex, hydrogels, polystyrene and liposomes. The beads can have added surface groups to facilitate attaching reporter molecules, such as carboxyl groups on latex and amino-modified polystyrene.

A wide range of bead sizes can be utilized in this invention. It is preferred that the reporter beads be uniform in size and in number of attached reporter molecules so that the fluorescence intensity is uniform. It is preferred that the diameters are uniform to within 2%. Currently available beads having diameters <20 μm are sufficiently homogeneous. In order to accommodate enough reporter molecules to reliably measure the fluorescence, the diameter of the substrate beads is typically >100 nm. For use in a flow cytometer having narrow flow channels, the bead size should be compatible with the channel size. If, for example, the channel size is designed to accommodate 3 μm diameter cells, the beads are preferably <3 μm in diameter.

Various techniques can be employed to immobilize the reporter molecules on the substrate bead. Adsorption-based coatings can be prepared by immersing the substrate beads in a reporter molecule solution and then washing off excess reporter molecules. Reporter molecules can similarly be diffused into the cavity of controlled pore glass beads. Reporter molecules can also be covalently immobilized by chemically attaching them to functional groups of suitable substrate beads. Polymerized beads can be formed in a solution containing reporter molecules, thereby trapping the molecules in a fixed polymer cavity. To immobilize reporter molecules in a liposome, lipids can be mixed with a reporter molecule solution, the solution shaken, and the liposomes separated.

To use the reporter beads of this invention, the beads are mixed with a fluid sample and the fluorescence of individual beads is measured. The beads can be dry before mixing with the sample or can be dispersed in a fluid. For microscale measurements it is preferred that the added volume of beads and any accompanying fluid be small compared to the sample volume (for example <1%) so that sample dilution is insignificant. The number of beads need not be precisely determined because the fluorescence of individual beads is measured as opposed to the total fluorescence of the mixture. Although only the measurement of a single bead is required, typically the fluorescence from many beads is signal averaged. For rapid measurement, the number of beads mixed with the sample fluid is preferably sufficient to have at least 50 beads/min flow through the measurement zone, and more preferably about 1000 beads/min. In order to avoid having two beads simultaneously in the measurement zone, the volume of beads is typically <0.2% of the volume of sample fluid. It is also possible to compensate for measuring two beads at the same time by algorithmically identifying and removing the associated fluorescence intensity from the data set.

Figure 2:
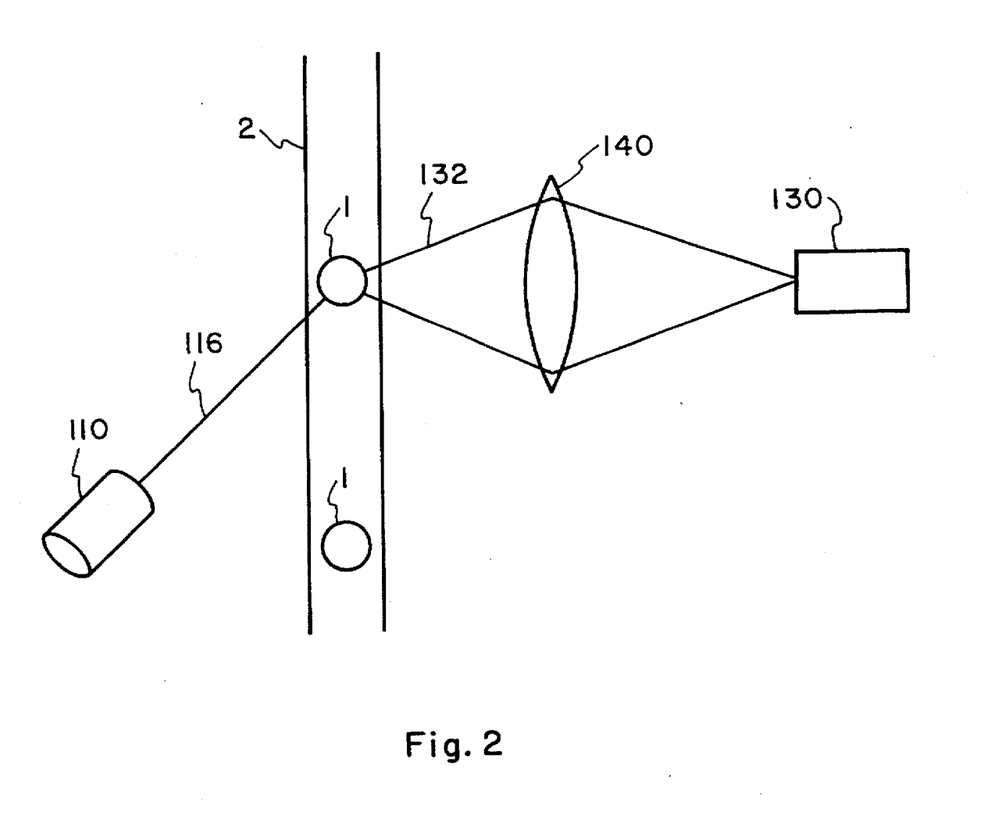
FIG. 2 shows fluorescence measurement of a reporter bead of this invention.

Fluorescence from individual beads is measured in a flow cytometer. The term flow cytometer is used herein for any apparatus which creates a single file flow of particles within a fluid and measures fluorescence from the particles. The sample fluid can be constrained within a narrow flow channel or by hydrodynamic focussing within a sheath fluid. Fluorescence measurement of the reporter beads of this invention is illustrated in FIG. 2. Reporter beads 1 are dispersed in sample fluid 2. In the measurement zone, the beads are illuminated by excitation beam 116 from light source 110. Fluorescence 132 is collected by lens 140 and focussed on photodetector 130. Typically the fluorescence collection is orthogonal to the excitation beam. A myriad of light sources and photodetectors are known in the flow cytometer art. The light source is selected to provide the appropriate excitation wavelength for the reporter molecules being used and the photodetector is selected to be responsive to the reporter molecule fluorescence wavelength. A wavelength selective filter can be positioned before the photodetector.

To simultaneously measure a plurality of fluid bulk analytes, a mixture of different types of reporter beads can be used. Alternatively, more than one type of reporter molecule can be immobilized on a single bead. A mixture of reporter beads can contain, for example, $O_2$ sensitive beads and $CO_2$ sensitive beads, or $Na^+$ sensitive beads and $K^+$ sensitive beads. Since many of the reporter beads are at least weakly sensitive to pH, it is useful to include specifically pH sensitive beads within a mixture in order to normalize the fluorescence from the other reporter beads.

During measurement, the different types of reporter beads in a mixture can be distinguished based on fluorescence wavelength or bead size. Fluorescence at different wavelengths can be separated using dichroic beam splitters to direct light to different detectors. Additional measurement stations can be added in parallel or in series, each station having an excitation beam and a photodetector. Different reporter molecules having different excitation spectra can be distinguished by using different excitation wavelengths at different stations. To distinguish between reporter beads of different sizes, the flow cytometer can include small and/or large angle scattering detectors to determine bead size and the fluorescence detection can be gated to the bead size. Different reporter beads can also be identified by attaching to the reporter bead a chemically insensitive fluorescent marker molecule having a characteristic fluorescence emission different from the reporter molecule.

This invention further includes reporter bead cartridges. A bead cartridge comprises a cartridge with reporter beads disposed therein. Bead cartridges can be inserted in the fluid inlet of the flow cytometer, whereby the beads mix with the sample fluid as it flows through the cartridge. The term cartridge is used herein for a container which can hold reporter beads and which can be coupled with a fluid inlet. Bead cartridges can be employed because the fluorescence of the reporter beads of this invention does not depend on the exact concentration of reporter beads. Bead cartridges simplify the analysis by eliminating the sample preparation steps of measuring and adding reagents.

Figure 3:
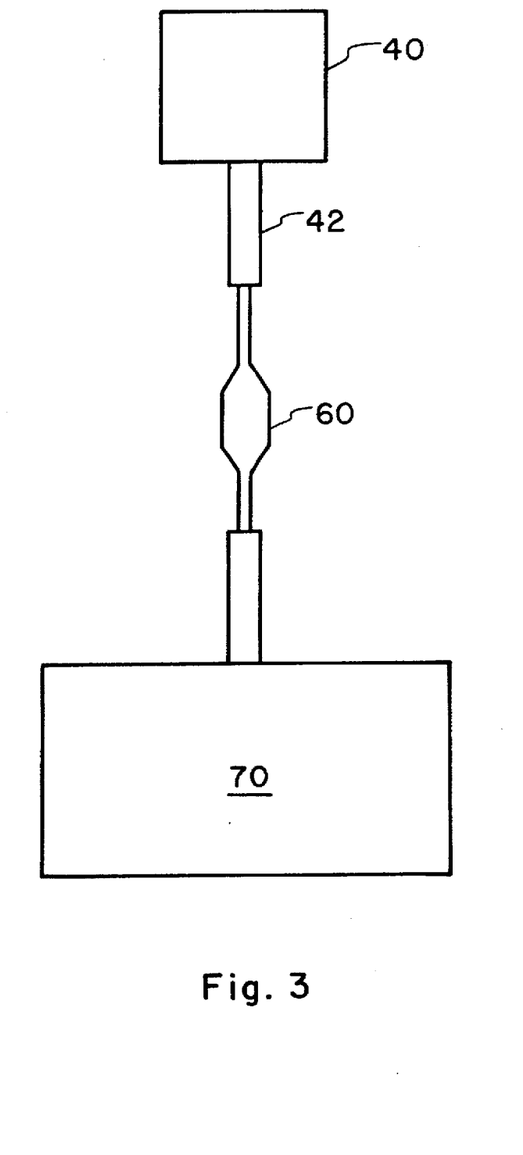
FIG. 3 shows a bead cartridge in the fluid inlet of a flow cytometer.

The bead cartridge can be positioned in the fluid inlet line as shown in FIG. 3. Sample fluid from container 40 flows through inlet line 42 to flow cytometer 70. Bead cartridge 60 is positioned in the fluid inlet line. The beads mix with the sample fluid as it flows through the cartridge. The fluid flow within the cartridge can be designed to facilitate mixing. Optionally, additional means for mixing can be included such as ultrasonic mixing. The bead cartridge can contain a single type of reporter bead or can contain more than one type. A plurality of bead cartridges, each containing a different type of reporter bead, can be used in series or in parallel.

Figure 4:
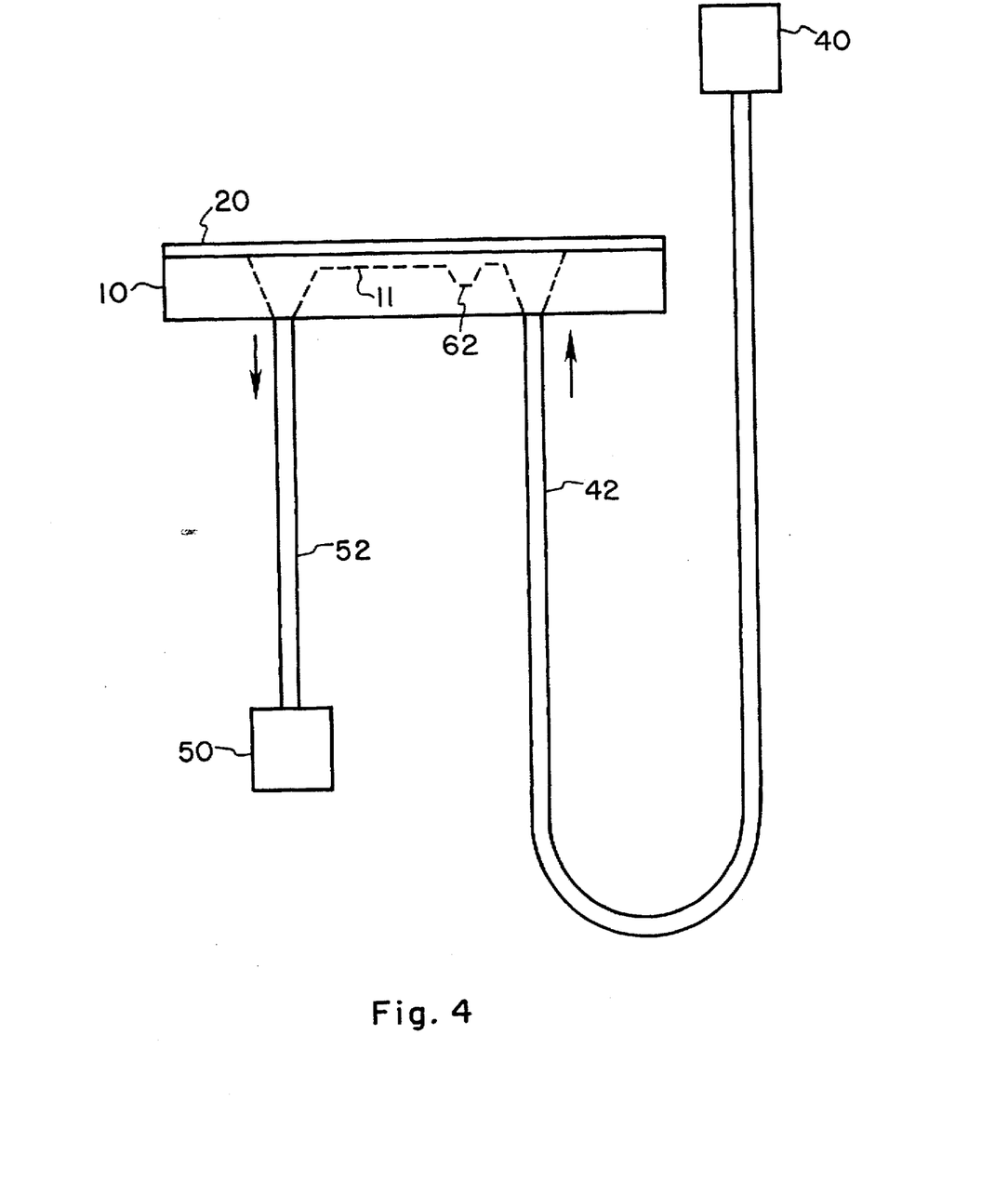
FIG. 4 shows a flow cytometer flow module having an integral bead cartridge.

This invention further provides a flow cytometer flow module having an integral bead cartridge, as illustrated in FIG. 4. In this embodiment the flow module, comprising wafer 10 and transparent cover plate 20, is a disposable flow module. Bead cartridge 62 is formed within the flow module and filled with reporter beads. In the illustrated embodiment, the cartridge is a widening and deepening of the flow channel. Alternative shapes and positionings can be employed. For example, the cartridge can be connected to the flow channel rather than being an integral part thereof. In use, sample fluid from container 40 flows through inlet line 42, mixes with the reporter beads in cartridge 62, flows through channel 11 for fluorescence measurement, and exits through outlet line 52 to receptacle 50. After use, the entire flow module, including the bead cartridge, is replaced. The fluorescence measurement is performed by a flow cytometer optical head, coupled to the flow module, having a fluorescence excitation source and a fluorescence detector. The optical head and the flow module in combination form a flow cytometer.

In the preferred embodiment wafer 10 is a silicon wafer and flow channel 11 is a V-groove etched therein. A detailed description of the V-groove flow channel is given in U.S. patent application Ser. No. 08/534,515, filed Sep. 27, 1995, which is incorporated by reference in its entirety herein. The V-groove flow channel is further illustrated in FIG. 5. Particle-containing sample fluid flows through the channel defined by V-groove groove 11 and cover plate 20. In the measurement zone, the sample fluid contains reporter beads 1 from the bead cartridge and, depending on the sample fluid, may also contain cells 3. The width of the top of the V-groove, w, is preferably small enough to force the particles into single file but large enough to pass the largest particles without clogging.

In an alternative embodiment, the sample fluid is hydrodynamically focused using a sheath flow. As is known in the art, for hydrodynamic focussing the sample fluid is injected into a stream of the sheath fluid and then the flow channel is constricted to reduce the diameter of the sample core. In this case the width of the channel at the measurement zone is many times larger than the largest particle. Hydrodynamic focussing has the advantage of reducing channel clogging, but requires a more complex fluid inlet system.

Figure 5:
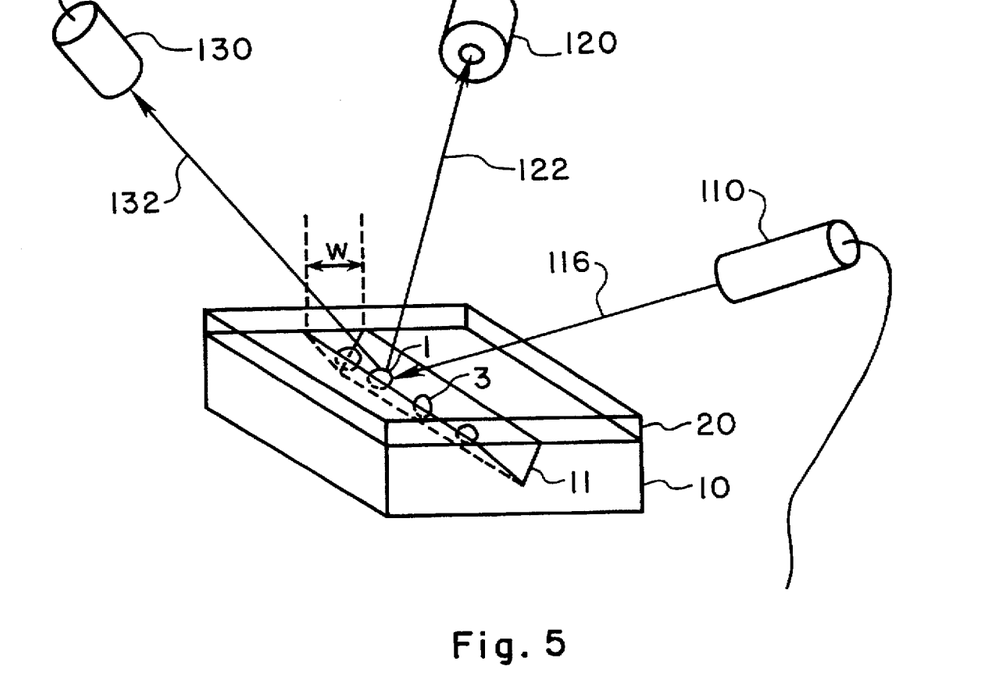
FIG. 5 shows reporter bead in a V-groove flow channel of a flow cytometer.

Optical measurement using the flow module of this invention is illustrated in FIG. 5. In the flow cytometer optical head, laser 110 provides illuminating laser beam 116. Fluorescence from the reporter beads, as well as large angle scattered light, travels along path 132 to large angle detector 130. The detector can contain a means, such as a spectrometer or a dichroic beamsplitter, for separating the excitation wavelength from the fluorescence wavelength. The flow cytometer optical head can further include small angle photodetector 120 positioned on path 122. One embodiment of the flow module with an integral bead cartridge has been illustrated herein; the bead cartridge of this invention can also be incorporated into other flow module designs.

Preferred embodiments of the reporter beads, bead cartridge and flow module of this invention have been described above. Numerous other embodiments will be readily apparent to those skilled in the art and fall within the range and scope of this invention.

For illustration, working examples of the reporter beads of this invention are described below.

EXAMPLE 1

Oxygen Sensitive Beads

Reporter beads of this invention were fabricated wherein oxygen sensing was based on the quenching of the fluorescence of a reporter molecule by molecular oxygen. The reporter molecule was ruthenium(II)-tris-(4,7-diphenyl-1,10-phenanthroline)-diperchlorate dye, having an excitation maximum of 465 nm, an emission maximum of 565 nm, and a fluorescence decay time constant of 5 ms. The dye was adsorbed on polystyrene beads having a nominal diameter of 5 μm ±2.5%. In addition, 10 μm beads have been employed. The adsorption process was accomplished successfully in either methanol, or in a bicarbonate buffer solution.

Synthesis of the indicator dye ruthenium(II)-tris-(4,7-diphenyl-1,10-phenanthroline)-diperchlorate was performed as follows. 451.8 mg $RuCl_3H_2O$ were dissolved in 10 ml ethylene glycol and 1 ml $H_2O$ and heated to 160° C. The color changed from orange to blue green. The mixture was cooled to 120° C., and 1726 mg of 4,7-diphenyl-1,10-phenanthroline were added. The mixture was heated under reflux at 160° C. for 45 min. After cooling to room temperature, 100 ml acetone were added and filtered through a G4 glass filter. The filtrate contained the complex as impure chloride.

100 ml of 1M perchloric acid, followed by 100 ml water, were added to 20 ml of the filtrate. This caused the precipitation of the dye complexes. The complexes were filtered in a G4 glass filter and washed several times with water. Then the complexes were dried under vacuum. The dry complexes were dissolved in a water/acetone mixture (1:4), recrystallized, and dried again, resulting in red-orange crystals.

Adsorption of the dye on polystyrene beads was successfully accomplished by the two different methods tested. For adsorption in methanol, the following procedure was used. 0.5 ml of a 2.5% solids aqueous polystyrene bead solution of a nominal diameter of 5 mm±2.5% were centrifuged. The excess water was removed, and the beads were dried completely. The dry beads were then suspended in 1 ml of a methanol solution in which 10 mg of ruthenium(II)-tris-(4,7-diphenyl-1,10-phenanthroline)-diperchlorate were suspended. The mixture was placed in an ultrasonic bath at 50° C. for 12 hours. Then the suspension was centrifuged, and two solid and one liquid phases formed. The liquid (methanol) was removed. The upper, lightly orange colored solid layer contained the polystyrene beads with adsorbed oxygen indicator dye. The lower layer contained excess indicator dye. The upper layer was removed with a Pasteur pipette and resuspended in 1 ml of methanol. The beads were then washed five times with methanol and five times with water.

Adsorption in bicarbonate buffer was performed as follows. 0.5 ml of a 2.5% solids aqueous polystyrene bead solution of a nominal diameter of 5 mm±2.5% were centrifuged. The excess water was removed, and the beads were resuspended in 1 ml of a 0.1M bicarbonate buffer of pH 8.5. The centrifugation and resuspension were repeated twice. Then, 50 mg of ruthenium(II)-tris-(4,7-diphenyl-1,10-phenanthroline)-diperchlorate were added to the suspension. The mixture was placed in an ultrasonic bath at 50° C. for 24 hours. Then the suspension was centrifuged, and two solid and one liquid phases formed. The liquid (bicarbonate buffer) was removed. The upper, orange colored solid layer contained the polystyrene beads with adsorbed oxygen indicator dye. The lower layer contained excess indicator dye.

The upper layer was removed with a Pasteur pipette and resuspended in 1 ml of 0.1M bicarbonate buffer of pH 8.5. The beads were then washed five times with bicarbonate buffer and five times with water.

The fluorescence of suspensions of $O_2$-sensitive reporter beads was observed qualitatively. Three batches of suspensions of the oxygen-reporter beads in de-ionized water (0.1% solids) were prepared. One suspension was equilibrated with pure nitrogen by bubbling nitrogen through the suspension, the others were equilibrated with air (20.9% oxygen), and with pure oxygen. Drops of each suspension were then placed next to each other on a microscopic slide. The slide was observed with a fluorescence microscope set to an excitation wavelength of 488 nm, and emission window of >520 nm. The fluorescence intensity of the beads in the droplet equilibrated with nitrogen was the brightest, the droplet equilibrated with air was the next brightest, and the droplet equilibrated with oxygen had the least fluorescence intensity. After about 20 minutes, the reporter beads in each drop assumed about the fluorescence intensity of the ones in the drop equilibrated with air, presumably because of the exposure of all drops to surrounding air and eventual equilibration.

EXAMPLE 2 pH Sensitive Beads pH sensitive beads were prepared by immobilizing the dextrane-coupled dye Carboxy SNAFL-1 (Molecular probes) on amino-modified polystyrene beads of 6 μm diameter. The procedure was performed by Molecular Probes. Two batches of suspensions of the pH reporter beads in buffer were prepared, one in Hepes 0.1M, pH 8.0, and one in Hepes 0.1M, pH 6.0, both 0.1% solids. Drops of each suspension were then placed next to each other on a microscopic slide. When observing the slide with a fluorescence microscope set to an excitation wavelength of 488 nm and emission window of >510 nm, the fluorescence intensity of the beads immersed in the buffer of pH 8.0 was much stronger than the intensity of the beads in the pH 6.0 suspension.

EXAMPLE 3

$CO_2$ Sensitive Beads

Liposomes (diameter roughly 600 nm) were generated with lipids in a solution containing 1 mg/3 ml of carboxy SNAFL-1 (Molecular probes) in a buffer (Hepes 0.1M, pH 8.0). The liposomes were washed on a column using pure Hepes 0.1M, pH 8.0 buffer until the eluent showed no more fluorescence. Two batches of suspensions of the carbon dioxide reporter beads in buffer (Hepes 0.1M, pH 8.0), (0.1% solids) were prepared. One suspension was equilibrated with pure nitrogen by bubbling nitrogen through the suspension, the other was equilibrated with pure carbon dioxide. Drops of each suspension were then placed next to each other on a microscopic slide. When observing the slide with a fluorescence microscope set to an excitation wavelength of 488 nm and emission window of >520 nm, the fluorescence of the beads in the droplet equilibrated with nitrogen was stronger than the fluorescence of the one equilibrated with carbon dioxide.

TABLE 1

Reporter Beads

| Analyte | Reporter Molecule | Substrate Bead |
|---|---|---|
| $O_2$ | ruthenium diphenyl phenanthroline | polystyrene |
| $CO_2$ | pH sensitive dye | liposomes |
| pH | Carboxy SNARF-1 or Carboxy SNAFL-1[1] | amino-modified polystyrene |
| $Ca^{+2}$ | Fura3 FF[1] | amino-modified polystyrene |
| $Na^+$ | Sodium-Green[1] | polystyrene |
| $K^+$ | Potassium-Green[1] | polystyrene |
| Cl | Lucigenin[1] | polystyrene |
| albumin | Albumin Blue 580[1] | polystyrene |

[1]Molecular Probes, Inc., Eugene Oregon

We claim:

1. A method of measuring the concentration of a first analyte in the fluid bulk of a sample fluid, comprising the steps of:

mixing a plurality of a first type of reporter beads with said sample fluid, each said reporter bead comprising:
a substrate bead; and
a plurality of a first type of reporter molecule immobilized on or in said substrate bead;
wherein an optical property of said reporter molecules is a function of the concentration of said first analyte;

flowing said sample fluid through the measurement zone of a flow cytometer such that said reporter beads flow in substantially a single file;

measuring said optical property of said reporter molecules; and obtaining the concentration of said first analyte from said optical property.

2. The method of claim 1 wherein said optical property is fluorescence.

3. The method of claim 1 wherein said optical property is absorbance.

4. The method of claim 1 wherein said sample fluid comprises first and second analytes, and wherein said first type of reporter molecule is intentionally sensitive to said first analyte and incidentally sensitive to said second analyte, and wherein said reporter bead further comprises a plurality of a second type of reporter molecules immobilized on or in said substrate bead, said second type of reporter molecules having an optical property which is a function of the concentration of said second analyte, said method further comprising the step of measuring said optical property of said second type of reporter molecules, and wherein said step of obtaining the concentration of said first analyte includes cross-sensitivity compensation by normalizing the optical signal from said first type of reporter molecules to the optical signal from said second type of reporter molecules.

5. The method of claim 1 wherein said sample fluid comprises first and second analytes, and wherein said first type of reporter molecule is intentionally sensitive to said first analyte and incidentally sensitive to said second analyte, and wherein said step of mixing comprises mixing both said first type of reporter beads and a second type of reporter beads with said sample fluid, each of said second type of reporter beads comprising:

a substrate bead; and
a plurality of a second type of reporter molecule immobilized on or in said substrate bead;
wherein an optical property of said second type of reporter molecules is a function of the concentration of said second analyte;

said method further comprising the step of measuring said optical property of said second type of reporter molecules, and wherein said step of obtaining the concentration of said first analyte includes cross-sensitivity compensation by normalizing the optical signal from said first type of reporter molecules to the optical signal from said second type of reporter molecules.

6. The method of claim 1 wherein said step of flowing follows said step of mixing without intervening incubation of said reporter beads in said sample fluid.

7. The method of claim 1 wherein said step of mixing does not include precisely measuring the volume of said sample fluid.

8. The method of claim 1 wherein said substrate bead is selected from the group consisting of glass, latex, hydrogel, polystyrene, liposome and polymer beads.

9. The method of claim 1 wherein said first type of reporter molecule is selected from the group consisting of pH, $O_2$, $CO_2$, $Ca^{+2}$, $Na^+$, $K^+$, $Cl^-$ and albumin sensitive molecules.

10. The method of claim 1 wherein said first type of reporter molecule is a halide sensitive molecule.

11. The method of claim 1 wherein said first type of reporter molecule is a metal ion sensitive molecule.

12. The method of claim 1 wherein said first type of reporter molecule is a alkali metal ion sensitive molecule.

13. The method of claim 1 wherein said first type of reporter molecule is a alkaline-earth metal ion sensitive molecule.

14. The method of claim 1 wherein said first type of reporter molecule is a drug sensitive molecule.

15. The method of claim 1 wherein said first type of reporter molecule is a pesticide sensitive molecule.

16. The method of claim 1 wherein said first type of reporter molecule is a alcohol sensitive molecule.

17. The method of claim 1 wherein said first type of reporter molecule is a sugar sensitive molecule.

18. The method of claim 1 wherein said first type of reporter molecule is an organic salt sensitive molecule.

19. The method of claim 1 wherein said first type of reporter molecule is a pH sensitive molecule and wherein said substrate bead is a polystyrene bead.

20. The method of claim 1 wherein said first type of reporter molecule is a pH sensitive molecule and wherein said substrate bead is a liposome.

21. The method of claim 1 wherein said first type of reporter molecule is an $O_2$ sensitive molecule and wherein said substrate bead is a polystyrene bead.

22. The method of claim 1 wherein the response time of said optical property to said analyte is less than one second.

23. The method of claim 1 wherein said reporter bead does not, in said fluid bulk, form an aggregate with other particles.

24. The method of claim 1 wherein only one of said reporter beads flows through said measurement zone at a time.

25. The method of claim 1 wherein said reporter beads do not have immunoreagents thereon.

26. The method of claim 1 wherein said fluorescence changes by at least 10% over the analytical range of said concentration of said analyte.

27. The method of claim 1 wherein said fluorescence changes by at least 50% over the analytical range of said concentration of said analyte.

28. A reporter bead cartridge for adding reporter beads to a sample fluid as said fluid is inlet into a flow cytometer, said reporter beads for detection of an analyte in the fluid bulk of said sample fluid, said bead cartridge comprising:

a cartridge adapted for coupling with the fluid inlet of the flow cytometer, whereby reporter beads disposed therein mix with the sample fluid as it flows through the cartridge and into the flow cytometer; and a plurality of reporter beads disposed within said cartridge, each reporter bead comprising:
a substrate bead; and
a plurality of a first type of reporter molecule immobilized on or in said substrate bead;
wherein an optical property of said reporter molecules is a function of the concentration of said analyte in said fluid bulk.

29. The bead cartridge of claim 28 further comprising a plurality of a second type of reporter beads disposed within said cartridge, said second type of reporter beads for measurement of a second analyte in said fluid bulk, each of said second type of reporter beads comprising:
a substrate bead; and
a plurality of a second type of reporter molecule immobilized on or in said substrate bead;
wherein a fluorescence property of said second type of reporter molecule is a function of the concentration of said second analyte.

30. The bead cartridge of claim 29 wherein said second type of reporter molecule is a pH sensitive molecule.

31. A disposable flow module for use with a flow cytometer optical head, comprising:
a flow channel;
a fluid inlet coupled to a first end of said flow channel;
a bead cartridge as recited in claim 28 coupled to said fluid inlet; and
a fluid outlet coupled to a second end of said flow channel.

32. The flow module of claim 31 wherein said flow channel is formed in a silicon wafer.

33. The flow module of claim 32 wherein said cartridge is formed in said silicon wafer.

34. The flow module of claim 32 wherein said cartridge is connected to said silicon wafer.

35. The flow module of claim 32 wherein said flow channel comprises a silicon wafer having a V-groove in the surface thereof.

36. The flow module of claim 31 wherein said flow channel is a microchannel.

37. The flow module of claim 31 wherein said module further includes means for hydrodynamically focussing said sample fluid.

38. A cross-sensitivity compensating reporter bead for optical detection of a first analyte in a fluid bulk also containing a second analyte, using a reporter molecule which is intentionally sensitive to said first analyte and incidentally sensitive to said second analyte, comprising:
a substrate bead;
a plurality of a first type of reporter molecules immobilized on or in said substrate bead, wherein an optical property of said first reporter molecules is a function of the concentrations of both said first analyte and said second analyte; and
a plurality of a second type of reporter molecule immobilized on or in said substrate beads, wherein an optical property of said second reporter molecules is a function of the concentration of said second analyte.

39. The reporter bead of claim 38 wherein said second analyte is selected from the group consisting of hydrogen ions, dissolved oxygen and solvent polarity.

40. The reporter bead of claim 39 wherein said second analyte is hydrogen ions.

41. A cross-sensitivity compensating reporter bead mixture for optical measurement of the concentration of a first analyte in a fluid bulk also containing a second analyte, using a reporter molecule which is intentionally sensitive to said first analyte and incidentally sensitive to said second analyte, said mixture comprising:

a plurality of a first type of reporter bead, each said bead comprising:

a first type of substrate bead; and a plurality of a first type of reporter molecule immobilized on or in said substrate bead, wherein an optical property of said first type of reporter molecules is a function of the concentrations of both said first analyte and said second analyte; and a plurality of a second type of reporter bead, each said bead comprising:

a second type of substrate bead; and a plurality of a second type of reporter molecule immobilized on or in said substrate bead, wherein an optical property of said second reporter molecules is a function of the concentration of said second analyte 42. The reporter bead mixture of claim 41 wherein said second analyte is selected from the group consisting of hydrogen ions, dissolved oxygen and solvent polarity.

43. The reporter bead of claim 42 wherein said second analyte is hydrogen ions.

44. The bead mixture of claim 41 wherein said second type of reporter beads have a different diameter from said first type of reporter beads.

45. The bead mixture of claim 41 wherein said second type of reporter molecule has a different fluorescence spectrum from said first type of reporter molecule.

46. The bead mixture of claim 41 wherein each of said first type of reporter bead further comprises a first type of chemically insensitive fluorescent marker molecule immobilized thereon or therein.

47. The bead mixture of claim 38 wherein each of said second type of reporter bead further comprises a second type of chemically insensitive fluorescent marker molecule immobilized thereon or therein.

* * * * *